United States Patent [19]

Guglielmetti et al.

[11] Patent Number: 5,114,621
[45] Date of Patent: May 19, 1992

[54] INDOLINO-SPIRO-OXAZINE PHOTOCHROMIC COMPOUNDS WITH FIVE-MEMBERED RINGS, METHOD FOR THEIR PREPARATION, PHOTOCHROMIC COMPOSITIONS AND ARTICLES CONTAINING SUCH COMPOUNDS

[75] Inventors: Robert Guglielmetti; Pascale Tardieu, both of Marseille, France

[73] Assignee: Essilor International (Compagnie Generale d'Optique, Creteil, France

[21] Appl. No.: 532,325

[22] Filed: Jun. 5, 1990

[30] Foreign Application Priority Data

Jun. 5, 1989 [FR] France .................... 89 07402

[51] Int. Cl.$^5$ .................... G02B 5/23; F21V 9/04; C07D 265/00
[52] U.S. Cl. .................... 252/586; 252/589; 544/71
[58] Field of Search ............... 252/586, 582, 589, 587; 350/354; 544/71

[56] References Cited

U.S. PATENT DOCUMENTS 4,792,224 12/1988 Kwiatkowski et al. ............ 252/586

FOREIGN PATENT DOCUMENTS 0245020 11/1987 European Pat. Off. .
0313941 5/1989 European Pat. Off. .
8907104 8/1989 World Int. Prop. O. ............ 544/71

Primary Examiner—Robert L. Stoll
Assistant Examiner—Philip Tucker
Attorney, Agent, or Firm—Millen, White & Zelano

[57] ABSTRACT

The new photochromic compounds of the invention have the formula of an indolino-spiro-oxazine comprising an indolinic part and an oxazine part, wherein said oxazine part comprises an unsaturated heterocycle with 5 links which comprises one or several atoms selected from nitrogen and sulphur.

Preferably the heterocycle is orthocondensed with a benzenic ring of the oxazine part of the compound, and said heterocycle comprises an imine C=N-bond. The ozazine part may typically be comprised of a benzothiazol-oxazine group of of an indolino-oxazine group.

11 Claims, No Drawings

INDOLINO-SPIRO-OXAZINE PHOTOCHROMIC COMPOUNDS WITH FIVE-MEMBERED RINGS, METHOD FOR THEIR PREPARATION, PHOTOCHROMIC COMPOSITIONS AND ARTICLES CONTAINING SUCH COMPOUNDS

BACKGROUND OF THE INVENTION

The present invention concerns new photochromic compounds of the indolino-spiro-oxazine type, a method for their preparation, as well as compositions and articles with photochromic properties containing at least one of said photochromic coumpounds. Generally speaking the compounds of the present invention can be used advantageously in making all sorts of optical lenses, the term optical lens mainly referring to an ophthalmic lens, a contact lens, or a sun protection lens.

Photochromism is a well known reversible phenomenon which is illustrated typically by a compound which undergoes a change in color when exposed to light radiations, including those in the U. V. range, such as sunlight, and returns to its original color upon stopping light exposure.

Such compounds are useful for example in the manufacture of lenses for sunlight-protection glasses or in other applications involving the need for making the transparency of an article vary according to ambient light intensity. They can be applied onto a transparent support or incorporated within a transparent polymerized organic material, in combination with a large variety of polymer compositions.

A number of organic photochromic compounds having a formula including an indolino-spiro-oxazine group have already been provided for such uses, especially in the field of sunlight protection lenses.

U.S. Pat. Nos. 3,562,172 and 3,578,602 have thus disclosed compounds showing a photochromic effect which belong to the family of indolino-spiro-naphthoxazines, while U.S. Pat. No. 4,215,010 describes indolino-spironaphtoxazines wherein the naphthalene nucleus comprises methoxy, ethoxy or halogen substituents. Similar photochromic compounds comprising a pyrido-benzene nucleus instead of the naphthalene nucleus in the compounds above are described in U.S. Pat. No. 4,720,547, as well as in the international patent application WO 87/00524.

Nevertheless, the compounds described in that prior art do not fully satisfy all the qualities that one expects from them. Considering more specifically the scope of their uses in lenses for sunlight protection, the photochromic material obtained, whether from a solution of the photochromic compound or by incorporating it into an organic polymer, should show a number of properties concerning the photochromic effect in addition to its natural transparency and its compatibility with the materials currently used for such lenses.

In particular:

When it is irradiated in the range of its photosensitivity, its coloration should appear rapidly, within a time preferably of the order of a second, and it should disappear when irradiation is stopped with similar rapidity.

The material should be stable in time, as well in itself as in its photochromism. Thus, the compound should be able within the material, to support a great number of coloration, decoloration sequences throughout a long period of use which may extend to several years.

The colorability should be good for reasonable contents of the photochromic compounds, and the absorption spectrum of the irradiated material should cover the whole of the visible spectrum as far as possible.

The photochromic effect should preferably be independent of the substrate containing the compound and it should occur at all temperatures within a large range, i.e. at variable ambient temperatures as well as when it is heated under irradiation.

The coloration showed by the material under radiation should also answer to aesthetic requirements and preserve a pleasant sight of the surroundings for those wearing glasses or ophthalmic lenses made of such materials. From that point of view one should avoid the blue colors which are generally encountered with the compounds of the prior art above and green should be preferred.

SUMMARY OF THE INVENTION

In order to satisfy the various requirements better than with the known compounds, the invention provides new photochromic compounds which are characterized in that they show the formula of an indolino-spiro-oxazine comprising an indolinic part and an oxazine part, wherein the oxazine part comprises an unsaturate five heterocycle 5 links.

According to secondary features of the invention:

Said heterocycle comprises one or several hetero atoms selected from nitrogen and sulphur, and among such heterocycles those comprising at least one sulphur atoms, and more specifically those comprising a sulphur atom and a nitrogen atom, such as the thiazole nucleus, are preferred.

Said heterocycle is ortho condensed with a benzenic nucleus of the oxazine part of the compound, this part being of the benzo-oxazine type.

Said heterocycle includes an imine C=N-bond.

Said oxazine part is in particular, and preferably, of the type of benzothiazolo-oxazine, or indolenino/oxazine.

Said heterocycle includes an imine C=N-bond.

The different cycles (or rings) in the indoline and oxazine parts of the molecule may carry various substituents which do not affect the global photochromic properties of the compounds.

More specifically the new compounds according to the invention, have preferably one of the following developed formulae:

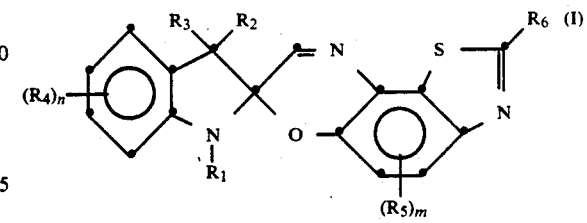

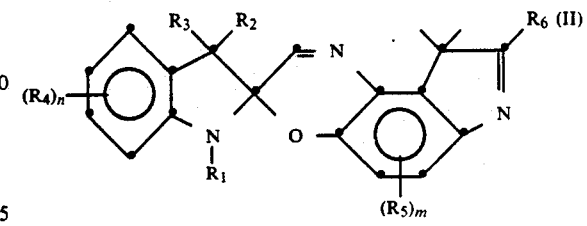

in each of which:
n varies from 0 to 4, m can be 1 or 2, $R_1$ is:

i) an alkyl group comprising from 1 to 16 carbon atoms such as the methyl, ethyl, n-propyl, isopropyl, n-butyl groups;

ii) a group selected from alkyl, phenyl, arylalkyl such as benzyl, phenyl which can be mono or di-substituted by alkyl or alkoxy substituents comprising from 1 to 6 carbon atoms;

iii) an alicyclic group such as a cyclohexyl group optionally substituted;

iv) an aliphatic hydrocarbon group comprising in its chain one or several hetero atoms such as O, N or S, in particular an acid, ether, or alcohol function;

$R_2$ and $R_3$ may each be, independently from each other, a $C_{1-8}$ alkyl group, a phenyl, phenyl mono or di-substituted with $C_{1-4}$ alkyl and/or $C_{1-5}$ alkoxy groups, or may be combined to form a cyclic ring comprising from 6 to 8 carbon atoms (including the spiranic carbon in the third position on the indolinic hetero cycle)

$R_4$ and $R_5$ can each be independently of each other:

i) a hydrogen atom, an amine function $NR'_1 R''$, wherein $R'$ and $R''$ each independently represent an hydrogen atom, an alkyl group, a cycloalkyl group, a phenyl group, or a substituted derivate there from; $R'$ and $R''$ may be combined to form a cycloalkyl group which can be substituted or contain one or several hetero atoms;

ii) a R, OR, SR, COR or COOR, group wherein R represents an hydrogen atom, an alkyl group comprising from 1 to 6 carbon atoms, or an aryl or heteroaryl group;

iii) an halogen atom, a $C_{1-4}$ mono-haloalkyl group, wherein the halogen can typically be Cl or Br, or a $C_{1-4}$ polyhaloalkyl group such as $CF_3$;

iv) —$NO_2$, CN, SCN,

Each one of the $R_4$ substituents can be present on any of the convenient carbon atoms on the indoline part of the photochromic compounds in the 4, 5, 6 and 7 positions when the other one is a hydrogen atom, whereas when n=2 it is preferred that the substituents be present in positions 4 and 5, 5 and 6, 4 and 6, or 6 and 7.

$R_6$ is an hydrogen atom, or a $C_{1-8}$ alkyl group, or a phenyl group optionally substituted, or a functional group such as the amino, carbonyl, or halogen groups.

Preferably:

$R_1$ is a $C_{1-4}$ alkyl, phenyl or benzyl group.

$R_2$ and $R_3$ are selected from the $C_{1-5}$ alkyl groups such as methyl, or ethyl, and the phenyl group, or they are combined to form a cyclohexyl group;

Each of the $R_4$ group is selected from the group comprising hydrogen, $C_{1-2}$ alkyl, chlorine, fluorine, $C_{1-2}$ trihaloalkyl and $C_{1-5}$ alkoxy;

$R_5$ is a hydrogen atom, or a $C_{1-4}$ alkoxy group, or a tertiary amine;

And $R_6$ is a hydrogen atom, or an alkyl group comprising from 1 to 4 carbon atoms.

Among the compounds of the invention of particular interest are the compounds wherein:

the oxazine part is of the type benzothiazolooxazine;

$R_1$ is a $C_{1-4}$ alkyl group such as methyl, or ethyl, isopropyl or n-butyl;

$R_2$ and $R_3$ are each independently either a methyl, or ethyl group;

$R_4$ is a hydrogen atom, a methyl, methoxy or chloro group;

$R_5$ is a hydrogen atom and $R_6$ is a methyl group.

The present invention further concerns a method for the preparation of the photochromic indolino-spirooxazine compounds represented by the formula (I), or (II).

It involves a general scheme for synthesizing indolino-spiro-oxazines which is known per se and which consists in condensing a Fischer's base, or a 2-alkylidenes indolinic compound with a nitroso-hydroxy heteroaromatic compound. As a first step the suitable nitrosohydroxy-hetero-aromatic compound such as a 7-nitroso 6-hydroxy-benzothiazole type for example, optionally substituted by one or several $R_5$ groups such as specified for formulae (I) and (II), can be prepared from a convenient methoxy compound by hydrolyzing it into the corresponding hydroxy derivate, then nitrosating the latter.

When using them for preparing photochromic compositions, the compounds according to the present invention can be dissolved into a suitable solvent such as toluene or ethanol so as to obtain a photochromic solution. The same photochromic compounds can also be dissolved within a polymer, a copolymer or a mixture of polymers dissolved in a suitable organic solvent.

They are thereby incorporated in compositions according to the present invention which can be applied on, or introduced in, a tranparent organic polymer material so as to obtain a photochromic transparent article. Preferably this material is a material of optical quality, and more particularly a material suitable for manufacturing ophthalmic lenses.

They can also enter into photochromic compositions which are also equally within the scope of the present invention and which can be used directly for constituting photochromic plastic films, boards or lenses such as lenses for sun glasses, sight finders, camera optics, and filters.

Examples of compositions which are suitable according to the invention for manufacturing photochromic transparent materials and articles, comprise one or several photochromic compounds according to the invention in combination with one or several of the following polymers: polymers from polyolallylcarbonate monomers, polyacrylates, polyalkyl-acrylates such as polymethyl methacrylate (PMMA), cellulose acetate, cellulose triacetate, cellulose propiono or butyro-acetate, polyvinyl acetate, polyvinyl alcohol, polyurethanes, polycarbonates, polyethylene-terephthalate, polystyrene, copolymers of styrene and methyl-methacrylate, acrylonitrile, polyvinylbutyral.

The amount of the photochromic compound (or the composition containing this compound) applied on, or introduced in the polymer material has no critical significance, and it depends generally from the desired color intensity under radiation and from the method used to incorporate and/or apply the photochromic compound. This method can be anyone within the high number of methods convenient for photochromic compounds known from the prior art, and among them typically the dissolution or dispersion of the compound in the basic composition of the material, or the application of a photochromic layer on the surface of/or inside a transparent support material.

Generally speaking the higher the amount of photochromic compound added, the more important the coloration under radiation. Such an amount can be described as a photochromic amount. Usually the amount of photochromic compound incorporated in the optical material is from 0.01 to 20% by weight, and preferably from 0.05 to 10% by weight, with respect to the total weight of the optical material.

Through the photochromic effects obtained thereby there appears a coloration under exposure to radiations within the U.V range, with the original color or transparency being recovered when the exposure to U.V. radiations is interrupted. This change in coloration can be renewed a high number of times, in accordance with what is required from sunlight protection lenses. Furthermore, the coloration remains all the time the material is exposed to sun radiations better than in the case of the photochromic compounds according to the prior art.

The invention will now be further illustrated by particular implementing examples which are not limiting.

EXAMPLE I

Step 1

1) 1 g of commercial 6-methoxy 2-methyl-benzothiazole thiazole ($5.5.10^{-3}$ moles) is mixed with 0.9 g of 48% azeotropic-hydro-bromic acid ($1.1\ 10^{-2}$ mole). The reaction is performed in a sealed tube at 125° C. during 6 hours. After neutralizing the solution with 3N ammonia (pH=7), the hydroxylated compound is extracted with chloroform. The yield is quantitative.

Melting point M. P.=147° C. ($C_8H_7NOS$, M+165).

2) A solution of $1.5\ 10^{-3}$ mole of the sodium nitrite in 3 ml water is added under stirring for one hour to a cooled solution (0°-5° C.) of $1.5\ 10^{-3}$ mole 6-hydroxy 2-methyl benzothiazole as obtained above, 0.3 ml concentrated hydrochloric acid and 3 ml distilled water. Stirring is continued for one hour at low temperature. The 6-hydroxy 7-nitroso 2-methyl benzothiazole is thus obtained as an orange precipitate which is washed with water, then dried.

Yield 55%, M. P.=215° C. ($C_8H_6N_2O_2S$, M=194).

Step 2

The intermediate compound resulting from the first step is used to prepare the photochromic compound of formula 1 wherein $R_4$ is H and $R_1$, $R_2$, $R_3$ are all $CH_3$ methyl groups as follows:

$1.4\ 10^{-3}$ mole of a Fischer's base 1,33, trimethyl-2-methylene indoline dissolved in 10 ml of n-heptane and 2 ml of dry ethanol are refluxed. At constant temperature nearby 76° C.) $1.4\ 10^{-3}$ mole of 6-hydroxy-7-nitroso-2-methyl benzothiazole of step 1 as a suspension in 12 ml of dry ethanol are slowly added in 2 hours.

The reaction mixture is maintained refluxing for 45 minutes. As the reaction is gradually developing, water is removed with ethanol by a Dean Stark Apparatus. Then 30 ml of ethanol are added up to a constant volume of solvent.

After passing the reaction mixture through a silica gel chromatographic column and removing the solvent, the solid residue is recrystallized in an appropriate mixture of apolar solvents such as petroleum ether, n-hexane, or benzene.

The product obtained is the indolino-spiro-oxazine compound of formula I, i.e. tri-methyl indolino-spiro-2-methyl-benzothiazolo-oxazine. The yield is about 50%, when the reaction solvent is a mixture of n-heptane and ethanol. Subsequent purification by recrystallization decreases the final yield to 40%.

EXAMPLE II

Under an inert hydrogen or argon atmosphere 1.4 ml of 1M solution of $BBr_3$ in dichloro-methane is added to a solution of $1.2\ 10^{-3}$ mole of 5-methoxy 2,3,3-trimethyl indolenine in 1.5 ml dichloromethane at 0° C. under stirring so as to obtain 5-hydroxy 2,3,3-trimethyl-indolenine.

The solution is stirred at ambient temperature and a precipitate appears. At the end of the reaction it is hydrolized with 0.1 N HCl.

One proceeds then with nitrozation according to the operating mode under 2 in step 1 of example I so as to obtain 4-nitroso 5-hydroxy 2,3,3-trimethyl-indolenine.

Following the same procedure as in step 2 of example I, and using the same indolinic Fischer's base the above compound is submitted to the spirannic condensation treatment.

There is thus obtained the trimethylindolino-spiroindolenino-oxazine with a yield of the order of 40%.

EXAMPLE III

Following the same procedure as in example I, one prepares the dimethyl isopropyl indolino-spiro 2-methyl benzothiazolo-oxazine compound corresponding to formula I wherein $R_2$, $R_3$ and $R_6$ are methyl groups, $R_1$ is an isopropyl group and $R_4$ and $R_5$ are hydrogen atoms.

EXAMPLE IV

Following the same procedure as in example I, one prepares the trimethyl 5-methoxy indolino-spiro 2-methyl benzothiazolo oxazine compound corresponding to formula I wherein $R_1$, $R_2$, $R_3$ and $R_6$ are methyl groups, $R_4$ is a methoxy group in the 5th position of the indoline cycle and $R_5$ is an hydrogen atom.

EXAMPLE V

The photochromic compounds obtained in the preceding examples are used for preparing polysiloxane varnishes of the type described in French Patent FR 82 0440, with the content of 1% by weight. The varnish obtained is applied on ophthalmic lenses made of organic material then hardened for to hours at 100° C. The thickness of the layers obtained is 2 microns. The percentage of the photochromic compound by weight in the hardened layer is about 5%.

EXAMPLE VI

The different compounds obtained in the preceding examples used as a solution in a solvent, at the same concentration in the various samples, are submitted to a coloration test under irradiation with comparison with photochromic compounds of the prior art. For each sample one measures the wave length corresponding to the maximum of the photocoloration range ($\lambda$max), or the limits of the photocoloration peak.

The results obtained are detailed thereafter:

| The prior art: | $\lambda$ max (nm) | Color |
|---|---|---|
| Trimethylindolino-spiro-benzo-oxazine | 590 | Blue |
| Homologue N-methoxyethyl | 606 | Blue |
| Homologue 6-methoxy N-methoxyethyl | 603 | Blue |
| Compounds of the invention: | Peak (nm) | Color |
| Example I | 621 | green blue |
| Example III | 626 | green blue |
| Example IV | 632 | green blue |

There is thus obtained thanks to the invention a displacement of the coloration appearing under irradiation towards the green color which is preferred for compounds intended for glasses or lenses for sunlight protection.

We claim:

1. A photochromic compound having one of the following formulae:

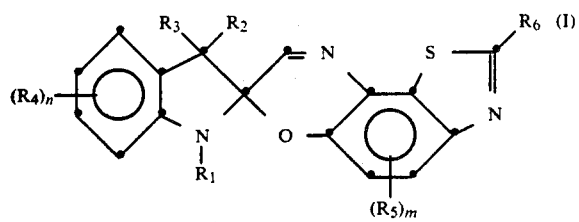

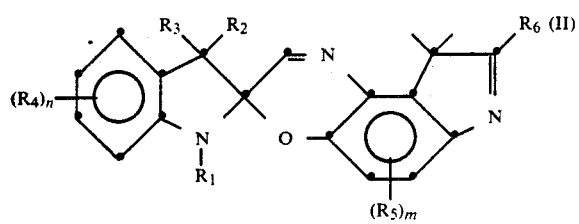

in each of which:

n is from 0 to 4, m is 1 or 2, $R_1$ is selected from:

i) an alkyl group of 1 to 16 carbon atoms;
  ii) a group selected from alkyl, phenyl, arylalkyl, phenyl or phenyl substituted with 1 or 2 substituents selected from alkyl and alkoxy comprising each from 1 to 6 carbon atoms;
  iii) an alicyclic group of up to 16 carbon atoms or;
  iv) an aliphatic hydrocarbon group of up to 16 carbon atoms comprising in its chain at least one hetero atom selected from O, N or S;

$R_2$ and $R_3$ are each independently from each other a $C_{1-8}$ alkyl group, phenyl, phenyl mono or di-substituted with at least one of $C_{1-4}$ alkyl and $C_{1-5}$ alkoxy group, or form together a cyclic ring comprising from 6 to 8 carbon atoms including the spiranic carbon in the third position of the indolinic hetero cycle;

$R_4$ and $R_5$ are independently from each other selected from:

i) a hydrogen atom or an amine group NR'R", wherein R' and R" each independently represent a hydrogen atom, an alkyl group, a cycloalkyl group, a phenyl group, or R' and R" form together a cycloalkyl group;
  ii) a group selected from R, OR, SR, COR and COOR, wherein R is a hydrogen atom, an alkyl group comprising from 1 to 6 carbon atoms, an aryl group or a heteroaryl group;
  iii) a halogen atom, a $C_{1-4}$ mono-haloalkyl group, wherein the halogen is chlorine or bromine, or a $C_{1-4}$ polyhaloalkyl group; and
  iv) $NO_2$, CN and SCN, and $R_6$ is a hydrogen atom, a $C_{1-8}$ alkyl group, a phenyl group or amino, carbonyl or halogen.

2. A photochromic compound according to claim 1, wherein:

$R_1$ is $C_{1-4}$ alkyl, phenyl or benzyl group;

$R_2$ and $R_3$ are selected from the $C_{1-5}$ alkyl groups such as methyl, or ethyl and the phenyl group, or they are combined to form a cyclohexyl group;

each of the $R_4$ group is selected from the group consisting of hydrogen, $C_{1-2}$ alkyl, chlorine, fluorine, $C_{1-2}$ trihaloalkyl and $C_{1-5}$ alkoxy;

$R_5$ is a hydrogen atom, or a $C_{1-4}$ alkoxy group, or a tertiary amine group; and $R_6$ is a hydrogen atom, or an alkyl group comprising from 1 to 4 carbon atoms.

3. A photochromic compound according to claim 1, wherein:

$R_1$ is a methyl or isopropyl group;

$R_2$ and $R_3$ are each a methyl group;

$R_4$ is a hydrogen or a methoxy group;

$R_5$ is hydrogen, and $R_6$ is a methyl group.

4. Compositions and articles which are photochromic under sunlight, comprising a compound according to claim 1 in the proportion from 0.01 to 20%.

5. Compositions and articles according to claim 4, said compound being in a proportion of 0.05 to 10% by weight.

6. A photochromic compound according to claim 1 of formula I.

7. A photochromic compound according to claim 1 of formula II.

8. A photochromic compound according to claim 2 of formula I.

9. A photochromic compound according to claim 3 of formula I.

10. A photochromic compound according to claim 2 of formula II.

11. A photochromic compound according to claim 3 of formula II.

* * * * *